United States Patent
Kinney et al.

(10) Patent No.: US 6,940,003 B1
(45) Date of Patent: Sep. 6, 2005

(54) PLAN LECITHIN: CHOLESTEROL ACYLTRANSFERASES

(75) Inventors: Anthony J. Kinney, Wilmington, DE (US); Karlene H. Butler, Newark, DE (US)

(73) Assignee: E. I. du Pont de Nemours and Company, Wilmington, DE (US)

(*) Notice: Subject to any disclaimer, the term of this patent is extended or adjusted under 35 U.S.C. 154(b) by 0 days.

(21) Appl. No.: 09/857,612

(22) PCT Filed: Dec. 2, 1999

(86) PCT No.: PCT/US99/28586

§ 371 (c)(1),
(2), (4) Date: Jun. 4, 2001

(87) PCT Pub. No.: WO00/32791

PCT Pub. Date: Jun. 8, 2000

Related U.S. Application Data

(60) Provisional application No. 60/110,782, filed on Dec. 3, 1998.

(51) Int. Cl.$^7$ .......................... A01H 1/00; C07H 21/04; C07K 14/415; C12N 5/14; C12N 9/00

(52) U.S. Cl. ...................... 800/295; 435/69.1; 435/468; 435/183; 435/235; 435/325; 435/410; 435/419; 435/252.3; 435/320.1; 530/370; 536/23.2; 536/23.6; 800/278; 800/295

(58) Field of Search .......................... 435/6, 69.1, 70.1, 435/71.1, 183, 410, 419, 252.3, 320.1; 530/370; 536/23.2, 23.6, 24.1; 800/278, 295

(56) References Cited

FOREIGN PATENT DOCUMENTS

WO 98/46767 A1 10/1998

OTHER PUBLICATIONS

EMBL Sequence Database Library Accession No.: D46513, Mar. 9, 1995, T. Sasaki et al., Rice cDNA from shoot.
EMBL Sequence Database Library Accession No.: AC004557, Apr. 15, 1998, P. Shinn et al., Genomic sequence for Arabidopsis thaliana BAC F17L21.
Craig H. Warden et al., J. Biol. Chem., vol. 264(36):21573–21581, 1989, Tissue–specific Expression, Developmental Regulation, and Chromosomal mapping of the lecithin: cholesterol acyltransferase gene.
Yukio Murata et al., J. Lipid Res., vol. 37:1616–1622, 1996, Cloning of rabbit LCAT cDNA:increase in LCAT mRNA abundance in the liver of cholesterol–fed rabbits.
EMBL Sequence Database Library Accession No.: AW147120, Nov. 4, 1999, V. Walbot, Maize ESTs from various cDNA libraries sequenced at stanford University.
National Center for Biotechnology Information General Identifier No. 998999, Sep. 27, 1995, P.A. Schindler et al., Site–specific detection and structural characterization of the glycosylation of human plasma proteins lecithin:cholesterol acyltransferase and apolipoprotein D using HPLC/electrospray mass spectrometry and sequential glycosidase digestion.
Patrick A. Schindler et al., Protein Science, vol. 4:791–803, 1995, Site–specific detection and structural characterization of the glycosylation of human plasma proteins lecithin:cholesterol acyltransferase and apolipoprotein D using HPLC/electrospray mass spectrometry and sequential glycosidase digestion.
National Center for Biotechnology Information General Indentifier No. 418623, Jun. 11, 1999, G. Meroni et al., Nucleotide sequence of the cDNA for lecithin:cholesterol acyltransferase (LCAT) from the rat.
G. Meroni et al., Nucl. Acids Res., vol. 18(17):5308, Nucleotide sequence of the cDNA for lecithin:cholesterol acyltransferase (LCAT) from the rat.
Jotun Hein, Meth. in Enzymol., vol. 183:626–645, 1990, Unified approach to alignment and phyogenise.
National Center for Biotechnology Information General Identifier No: 3935185, Dec. 1, 1998, P. Shinn et al., Genomic sequence for Arabidopsis thaliana BAC F17L21.
Mitsuhisa Manabe et al., J. Lipid Res., vol. 28:1206–1215, 1987, New substrate for determination of serum lecithin: cholesterol acyltransferase.
Sissel Rogne et al., The Isolation And Characterisation Of A cDNA Clone For Human Lecithin:Cholesterol Acyl Transferase And Its Use To Analyse The Genes in Patients With LCAT Deficiency And Fish Eye Disease, Biochemical and Biophysical Research Communications, vol. 148:161–169, 1987.

*Primary Examiner*—Phuong T. Bui

(57) ABSTRACT

This invention relates to an isolated nucleic acid fragment encoding a plant lecithin: cholesterol acyltransferases. The invention also relates to the construction of a chimeric gene encoding all or a portion of the plant lecithin:cholesterol acyltransferases in sense or antisense orientation, wherein expression of the chimeric gene results in production of altered levels of the plant lecithin:cholesterol acyltransferases in a transformed host cell.

14 Claims, 2 Drawing Sheets

```
Arabidopsis_(gi 3935185)   MKK-----I-SSHYSVVIAILVVTMTSMCQAVGSN------VYPLILVPGNGNQLEVR
corn_(SEQ ID NO:2)         MAR-IPQVLAPLLLLLLPAGLR--ELMIDRRPLPKRCRREVLLHPLVLVPGLTCSELDAR
corn_(SEQ ID NO:4)         MVHDMAS------CSRGGTIVLSKFASTTRRAPKQ------LPPVVVPGYATNELDAR
corn_(SEQ ID NO:6)         MASSLLQQLLSLLLLLPSPLRLREHLSGNHAVSAN------NEHPIFLVAGVSCSDLEAR
soybean_(SEQ ID NO:8)      MKKEQEEGL-KIEVATLTVTVVVMLSLLCTCGASN------LDPLILIPGNGNQLEAR Arabidopsis_(gi 3935185)   LDREYKPSSVWCSSWLYPIHKKSGGWFRLWEDAAVLLSPET-RCFSDRMMLYDPDLDDY
corn_(SEQ ID NO:2)         LTDAYRPFRAACDE-------GEGLVRLWTNCSDLPAHHYVRCFMEQMALVYDPVANDY
corn_(SEQ ID NO:4)         LTELYHPSSPRCA--------HKGKGWFRLYLNYTALEDAADVRCFAEQMATAYDAASDDY
corn_(SEQ ID NO:6)         LTEEYRPSVPHCGA-------MKGKGWFGLWKNSSELLSRDYVQCFEEQMSLVYDPAINEY
soybean_(SEQ ID NO:8)      LTNQYKPSTFICESW-YPLIKKKNGWFRLWFDSSVILAPFT-QCFAERMTLHYHQELDDY Arabidopsis_(gi 3935185)   QNAPGVQTRVPHFGSTKSLLYLDPRLRDATSYMEHLVKALEKKCGYVNDQTIL
corn_(SEQ ID NO:2)         RNLPGVETRVRNFGSSRGF-QKNPEHTTWSWCFEVLRNELARA-GYRDGDTLF
corn_(SEQ ID NO:4)         RNAQGVETRVPFFGSTRAFRYPDPDRRNF-SYMDKFVSRLERL-AYRDGENLF
corn_(SEQ ID NO:6)         RNLAGVETRVPNFGSTRAFSHKNPLKSD--WCLGKLRAALEDM-GYRDGDTMF
soybean_(SEQ ID NO:8)      FNTPGVETRVPHFGSTNSLLYLNPRLKHITGYMAPLVDSLQKL-GYADGETLF Arabidopsis_(gi 3935185)   GLAASGHPSRVASQFLQDLKQLVEKTSSENEGKPVILLS         LEVLHFLNRTTPSWR
corn_(SEQ ID NO:2)         APPVPGQPSRSSPATSVGWPSLVEDASRKNRGRKVILFG         MVALEFVRSTPMAWR
corn_(SEQ ID NO:4)         AVAPPGHPSRVADAFFGRLRRLVERASRANGGPVTIVA          TVAHQFLLRRPLPWR
corn_(SEQ ID NO:6)         APPSPGQTSEVYSRYFKELMELVEAASERTR-KKAVILG         MVALEFVRNTPPAWR
soybean_(SEQ ID NO:8)      GLAAEGHPSQVGSKFLKDLKNLIEEASNSNNGKPVILLS         LFVLQLLNRNPPSWR Arabidopsis_(gi 3935185)   RKYIKHFVALAAPW-GGTISQMKTFASGNTLG-VPLVNPL--LVRRHQRTSESNQWLLPS
corn_(SEQ ID NO:2)         DRYIKHLFLVAPVPAEGFVKPLQYFVSGSNLMYVPTVSSLEPAFRPMWRTFESSLVNFPS
corn_(SEQ ID NO:4)         RRFVRRFVPVAAPW-GGVVLGMLTIVAGNNLG-LPFVDPL--ALKGEYRSLQSSLWPLPN
corn_(SEQ ID NO:6)         REHIERLVLVAPTLPGGFLEPVRNFASGTDILYVPATTPLAT--RAMWRSFESAIVNFPS
soybean_(SEQ ID NO:8)      KKFIKHFIALSAPW-GGAIDEMYTFASGNTLG-VPLVDPL--LVRDEQRSSESNLWLLPN
```

FIG. 1A

```
Arabidopsis_(gi 3935185)       TKVFHDRTKPLVVTPQVNYTA--YEMDRFFADIGFSQGVVPYKTRVLPLTEELMTPGVPV
corn_(SEQ ID NO:2)             PAVFGR--RPLVVTARRNYSA--YDLEDLIVAVGYGAGVEPFRRRAVPKMSYFQAPMVPT
corn_(SEQ ID NO:4)             PNAFRA-GQPLVTTRSRTYTA--HDMADFLDAIGLGAAIVPYQSRVLPLFRELPSPRVPV
corn_(SEQ ID NO:6)             PAVFGRLQAPLVVTRERNYSASAHDMERFLAAVGSGEAAEPFRRRAVPKMGSFAAPMVPM
soybean_(SEQ ID NO:8)          PKIF-GPQKPIVITPIRPYSA--HDMVDFLKDIGFPEGVYPYETRILPLIGNIKAPQVPI Arabidopsis_(gi 3935185)       KQPEIK-          ASLAAL-------KVDS-LN
corn_(SEQ ID NO:2)             ATPEIV-          VSMLAFDEKMRRQPEQNKVYK
corn_(SEQ ID NO:4)             VTPMMV-          VSLLAVDP-AWRLPTA-Y-ER
corn_(SEQ ID NO:6)             AAPEVAA          ISVLAFEKEMRRQPEQKKQFK
soybean_(SEQ ID NO:8)          ERPEIS-          VSLLALQS-LWKEEKNQY-LK Arabidopsis_(gi 3935185)       TVEIDGVSHTSILKDEIALKEIMKQISIINY--ELANVNAVNE
corn_(SEQ ID NO:2)             SIKIRGAQHGTIVTDDTALKRVMHEILEANR--------S
corn_(SEQ ID NO:4)             MLKVRNVSHTGLFVDDAALAVIISAI--------LRPN
corn_(SEQ ID NO:6)             SIKINKAQHSTIVTDDFALHRVIQEIVEANNQK-----IPS
soybean_(SEQ ID NO:8)          VVKIDGVSHTSILKDEVALNEIVGEITSINSHAELGLSNLFSG
```

FIG. 1B

PLAN LECITHIN: CHOLESTEROL ACYLTRANSFERASES

This application claims the benefit of U.S. Provisional Application No. 60/110,782, filed Dec. 3, 1998.

FIELD OF THE INVENTION

This invention is in the field of plant molecular biology. More specifically, this invention pertains to nucleic acid fragments encoding plant lecithin:cholesterol acyltransferases in plants and seeds.

BACKGROUND OF THE INVENTION

Phosphatidylcholine-sterol O-acyltransferase (EC 2.3.1.43) transfers acyl groups from phosphatidylcholine to sterols. This enzyme is also known as lecithin:cholesterol acyltransferase (LCAT) and belongs to the class of CoA-independent acyltransferases. This enzyme is found associated with high-density lipoproteins (HDL) and forming a complex with its activators Apolipoprotein (apo)-A1 and apo-D. HDLs are believed to promote the process of reverse cholesterol transport. This process involves efflux of cellular cholesterol, cholesterol esterification and lipid transport and exchange. Apo A-1 and lecithin-cholesterol acyltransferase play a crucial role in reverse cholesterol transport.

The role of LCAT in plants will presumably be different from mammalian systems given the negligible levels of cholesterol found in plant oils. However, plants have a complex combination of membrane sterols that can change with environmental conditions as well as developmental determination. LCAT may function as the phosphatidylcholine acyl-exchange enzyme which moves unsaturated acyl groups into phosphatidylcholine for desaturation and out of it for incorporation into triacylglycerols. Overexpression of LCAT may lead to increased lipid metabolism and fluidity of membranes increasing resistance to heat and/or cold shock. Overexpression or cosuppression of LCAT may also be useful to genetically alter the content of phytosterol or lecithin in grains.

SUMMARY OF THE INVENTION

The present invention relates to isolated polynucleotides comprising a nucleotide sequence encoding a first polypeptide of at least 417 amino acids that has at least 60% identity based on the Clustal method of alignment when compared to a polypeptide selected from the group consisting of a corn plant lecithin:cholesterol acyltransferases polypeptide of SEQ ID NOs:2, 4, 8, 10, or 12, and a soybean plant lecithin:cholesterol acyltransferases polypeptide of SEQ ID NOs:6, or 14. The present invention also relates to an isolated polynucleotide comprising the complement of the nucleotide sequences described above.

It is preferred that the isolated polynucleotides of the claimed invention consists of a nucleic acid sequence selected from the group consisting of SEQ ID NOs:1, 3, 5, 7, 9, 11, and 13 that codes for the polypeptide selected from the group consisting of SEQ ID NOs:2, 4, 6, 8, 10, 12, and 14. The present invention also relates to an isolated polynucleotide comprising a nucleotide sequences of at least 60 (preferably at least 40, most preferably at least 30) contiguous nucleotides derived from a nucleotide sequence selected from the group consisting of SEQ ID NOs:1, 3, 5, 7, 9, 11, and 13 and the complement of such nucleotide sequences.

The present invention relates to an isolated polynucleotide comprising at least 30 contiguous nucleotides derived from a nucleotide sequence selected from the group consisting of SEQ ID NOs:1, 3, 5, 7, 9, 11, 13 and the complement of such sequences.

The present invention relates to a chimeric gene comprising an isolated polynucleotide of the present invention operably linked to suitable regulatory sequences.

The present invention relates to an isolated host cell comprising a chimeric gene of the present invention or an isolated polynucleotide of the present invention. The host cell may be eukaryotic, such as a yeast or a plant cell, or prokaryotic, such as a bacterial cell. The present invention also relates to a virus, preferably a baculovirus, comprising an isolated polynucleotide of the present invention or a chimeric gene of the present invention.

The present invention relates to a process for producing an isolated host cell comprising a chimeric gene of the present invention or an isolated polynucleotide of the present invention, the process comprising either transforming or transfecting an isolated compatible host cell with a chimeric gene or isolated polynucleotide of the present invention.

The present invention relates to a plant lecithin:cholesterol acyltransferases polypeptide of at least 417 amino acids comprising at least 60% homology based on the Clustal method of alignment compared to a polypeptide selected from the group consisting of SEQ ID NOs:2, 4, 6, 8, 10, 12, and 14.

The present invention relates to a method of selecting an isolated polynucleotide that affects the level of expression of a plant lecithin:cholesterol acyltransferases polypeptide in a host cell, preferably a plant cell, the method comprising the steps of:

constructing an isolated polynucleotide of the present invention or an isolated chimeric gene of the present invention;

introducing the isolated polynucleotide or the isolated chimeric gene into a host cell;

measuring the level a plant lecithin:cholesterol acyltransferases polypeptide in the host cell containing the isolated polynucleotide; and comparing the level of a plant lecithin:cholesterol acyltransferases polypeptide in the host cell containing the isolated polynucleotide with the level of a plant lecithin:cholesterol acyltransferases polypeptide in a host cell that does not contain the isolated polynucleotide.

The present invention relates to a method of obtaining a nucleic acid fragment encoding a substantial portion of a lecithin:cholesterol acyltransferases polypeptide gene, preferably a plant plant lecithin:cholesterol acyltransferases polypeptide gene, comprising the steps of: synthesizing an oligonucleotide primer comprising a nucleotide sequence of at least 60 (preferably at least 40, most preferably at least 30) contiguous nucleotides derived from a nucleotide sequence selected from the group consisting of SEQ ID NOs:1, 3, 5, 7, 9, 11, and 13 and the complement of such nucleotide sequences; and amplifying a nucleic acid fragment (preferably a cDNA inserted in a cloning vector) using the oligonucleotide primer. The amplified nucleic acid fragment preferably will encode a portion of a plant lecithin:cholesterol acyltransferases amino acid sequence.

The present invention also relates to a method of obtaining a nucleic acid fragment encoding all or a substantial portion of the amino acid sequence encoding a plant lecithin:cholesterol acyltransferases polypeptide comprising the steps of: probing a cDNA or genomic library with an isolated polynucleotide of the present invention; identifying a DNA clone that hybridizes with an isolated polynucleotide of the present invention; isolating the identified DNA clone; and sequencing the cDNA or genomic fragment that comprises the isolated DNA clone.

A further embodiment of the instant invention is a method for evaluating at least one compound for its ability to inhibit the activity of a plant lecithin:cholesterol acyltransferases, the method comprising the steps of: (a) transforming a host cell with a chimeric gene comprising a nucleic acid fragment encoding a plant lecithin:cholesterol acyltransferases, operably linked to suitable regulatory sequences; (b) growing the transformed host cell under conditions that are suitable for expression of the chimeric gene wherein expression of the chimeric gene results in production of plant lecithin:cholesterol acyltransferases in the transformed host cell; (c) optionally purifying the plant lecithin:cholesterol acyltransferases expressed by the transformed host cell; (d) treating the plant lecithin:cholesterol acyltransferases with a compound to be tested; and (e) comparing the activity of the plant lecithin:cholesterol acyltransferases that has been treated with a test compound to the activity of an untreated plant lecithin:cholesterol acyltransferases, thereby selecting compounds with potential for inhibitory activity.

BRIEF DESCRIPTION OF THE DRAWINGS AND SEQUENCE DESCRIPTIONS

The invention can be more fully understood from the following detailed description and the accompanying drawings and Sequence Listing which form a part of this application.

FIGS. 1A and 1B depict the amino acid sequence alignment between the lecithin:cholesterol acyltransferase corn clone cen3n.pk0141.f2:fis SEQ ID NO:8), corn clone cep1c.pk001.f7:fis (SEQ ID NO:10), corn clone chpc24.pk0001.c1 (SEQ ID NO:12), and soybean clone s12.pk0015.e8:fis (SEQ ID NO:14), with the *Arabidopsis thaliana* lecithin:cholesterol acyltransferase protein (NCBI General Identifier No. 3935185; SEQ ID NO:15). Conserved sequence elements are shown boxed in black with the amino acid sequence in white. The second boxed sequence (HS*G) contains a conserved serine that is believed to be the active site residue found in all serine lipases. This sequence motif is also conserved in mammalian lecithin:cholesterol acyltransferase (Rogne et al. (1987) *Biochem Biophys Res Commun* 148:161–169). All of the boxed sequences are largely conserved in the mammalian lecithin:cholesterol acyltransferase sequences.

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. The sequence descriptions and Sequence Listing attached hereto comply with the rules governing nucleotide and/or amino acid sequence disclosures in patent applications as set forth in 37 C.F.R. §1.821–1.825.

TABLE 1

Lecithin:Cholesterol Acyltransferases

| Lecithin: Cholesterol Acyltransferase (LCAT) | Clone Designation | SEQ ID NO: (Nucleotide) | SEQ ID NO: (Amino Acid) |
|---|---|---|---|
| maize [*Zea mays*] | cep1c.pk001.f7 | 1 | 2 |
| maize [*Zea mays*] | Contig of: chpc24.pk0001.c1 cbn2.pk0017.h4 cbn10.pk0052.g10 p0016.ctsbo30r p0018.chstj36r | 3 | 4 |
| soybean [*Glycine max*] | s12.pk0015.e8 | 5 | 6 |
| maize [*Zea mays*] | cen3n.pk0141.f2:fis | 7 | 8 |
| maize [*Zea mays*] | cep1c.pk001.f7:fis | 9 | 10 |
| maize [*Zea mays*] | chpc24.pk0001.c1 | 11 | 12 |
| soybean [*Glycine max*] | s12.pk0015.e8:fis | 13 | 14 |

The Sequence Listing contains the one letter code for nucleotide sequence characters and the three letter codes for amino acids as defined in conformity with the IUPAC-IUBMB standards described in *Nucleic Acids Res.* 13:3021–3030 (1985) and in the *Biochemical J.* 219 (No. 2):345–373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. As used herein, a "polynucleotide" is a nucleotide sequence such as a nucleic acid fragment. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. An isolated polynucleotide of the present invention may include at least 60 contiguous nucleotides, preferably at least 40 contiguous nucleotides, most preferably at least 30 contiguous nucleotides, of the nucleic acid sequence of the SEQ ID NOs:1, 3, 5, 7, 9, 11, 13, or the complement of such sequences.

As used herein. "contig" refers to a nucleotide sequence that is assembled from two or more constituent nucleotide sequences that share common or overlapping regions of sequence homology. For example, the nucleotide sequences of two or more nucleic acid fragments can be compared and aligned in order to identify common or overlapping sequences. Where common or overlapping sequences exist between two or more nucleic acid fragments, the sequences (and thus their corresponding nucleic acid fragments) can be assembled into a single contiguous nucleotide sequence.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-à-vis the ability to mediate gene silencing or alteration of the functional properties of the resulting protein molecule. It is therefore understood that the invention encompasses more than the specific exemplary nucleotide or amino acid sequences and includes functional equivalents thereof.

Substantially similar nucleic acid fragments may be selected by screening nucleic acid fragments representing subfragments or modifications of the nucleic acid fragments of the instant invention, wherein one or more nucleotides are substituted, deleted and/or inserted, for their ability to affect the level of the polypeptide encoded by the unmodified nucleic acid fragment in a plant or plant cell. For example, a substantially similar nucleic acid fragment representing at least 30 contiguous nucleotides derived from the instant nucleic acid fragment can be constructed and introduced into a plant or plant cell. The level of the polypeptide encoded by the unmodified nucleic acid fragment present in a plant or plant cell exposed to the substantially similar nucleic fragment can then be compared to the level of the polypeptide in a plant or plant cell that is not exposed to the substantially similar nucleic acid fragment.

For example, it is well known in the art that antisense suppression and co-suppression of gene expression may be accomplished using nucleic acid fragments representing less than the entire coding region of a gene, and by nucleic acid fragments that do not share 100% sequence identity with the gene to be suppressed. Moreover, alterations in a nucleic acid fragment which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. Consequently, an isolated polynucleotide comprising a nucleotide sequence of at least 60 (preferably at least 40, most preferably at least 30) contiguous nucleotides derived from a nucleotide sequence selected from the group consisting of SEQ ID NOs:1, 3, 5, 7, 9, 11, 13 and the complement of such nucleotide sequences may be used in methods of selecting an isolated polynucleotide that affects the expression of a polypeptide (such as lecithin:cholesterol acyltransferases) in a host cell. A method of selecting an isolated polynucleotide that affects the level of expression of a polypeptide in a host cell (eukaryotic, such as plant or yeast, prokaryotic such as bacterial, or viral) may comprise the steps of: constructing an isolated polynucleotide of the present invention or an isolated chimeric gene of the present invention; introducing the isolated polynucleotide or the isolated chimeric gene into a host cell; measuring the level a polypeptide in the host cell containing the isolated polynucleotide; and comparing the level of a polypeptide in the host cell containing the isolated polynucleotide with the level of a polypeptide in a host cell that does not contain the isolated polynucleotide.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (Hames and Higgins, Eds. (1985) Nucleic Acid Hybridisation, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6× SSC, 0.5% SDS at room temperature for 15 min. then repeated with 2× SSC, 0.5% SDS at 45° C. for 30 min, and then repeated twice with 0.2× SSC, 0.5% SDS at 50° C. for 30 min. A more preferred set of stringent conditions uses higher temperatures in which the washes are identical to those above except for the temperature of the final two 30 min washes in 0.2× SSC, 0.5% SDS was increased to 60° C. Another preferred set of highly stringent conditions uses two final washes in 0.1× SSC. 0.1% SDS at 65° C.

Substantially similar nucleic acid fragments of the instant invention may also be characterized by the percent identity of the amino acid sequences that they encode to the amino acid sequences disclosed herein, as determined by algorithms commonly employed by those skilled in this art. Suitable nucleic acid fragments (isolated polynucleotides of the present invention) encode polypeptides that are at least about 70% identical, preferably at least about 80% identical to the amino acid sequences reported herein. Preferred nucleic acid fragments encode amino acid sequences that are at least about 85% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95% identical to the amino acid sequences reported herein. Suitable nucleic acid fragments not only have the above homologies but typically encode a polypeptide having at least about 50 amino acids, preferably at least about 100 amino acids, more preferably at least about 150 amino acids, still more preferably at least about 200 amino acids, and most preferably at least about 250 amino acids. Sequence alignments and percent identity calculations were performed using the Megalign program of the LASERGENE bioinformatics computing suite (DNASTAR Inc. Madison, Wis.). Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) *J. Mol.*

*Biol.* 215:403–410). In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment "Chemically synthesized", as related to nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequence preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of plants* 15:1–82. It is further recognized that since in most cases the exact boundaries of regulatory sequences have not been completely defined, nucleic acid fragments of different lengths may have identical promoter activity.

The "translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Mol. Biotechnol.* 3:225–236).

The "3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post transcriptional processing of the primary transcript and is referred to as the mature RNA. "Messenger RNA (mRNA)" refers to the RNA that is without introns and that can be translated into polypeptide by the cell. "cDNA" refers to a double-stranded DNA that is complementary to and derived from mRNA. "Sense" RNA refers to an RNA transcript that includes the mRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

"Altered levels" refers to the production of gene product (s) in transgenic organisms in amounts or proportions that differ from that of normal or non-transformed organisms.

"Mature" protein refers to a post-translationally processed polypeptide; i.e. one from which any pre- or propeptides present in the primary translation product have been removed. "Precursor" protein refers to the primary product of translation of mRNA; i.e. with pre- and propeptides still present. Pre- and propeptides may be but are not limited to intacellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) *Ann. Rev. Plant Phys. Plant Mol. Biol.* 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al. (1987) *Meth. Enymol.* 143:277) and particle-accelerated or "gene gun" transformation technology (Klein et al. (1987) *Nature* (London) 327:70–73; U.S. Pat. No. 4,945,050, incorporated herein by reference).

Standard recombinant DNA and molecular cloning techniques used herein are well known in the art and are described more fully in Sambrook et al. *Molecular Cloning: A Laboratory Manual*; Cold Spring Harbor Laboratory Press: Cold Spring Harbor, 1989 (hereinafter "Maniatis").

Nucleic acid fragments encoding at least a portion of several plant lecithin:cholesterol acyltransferases have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other plant lecithin:cholesterol acyltransferases, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primer DNA labeling, nick translation, or end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) *Proc. Natl. Acad. Sci. USA* 85:8998–9002) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) *Proc. Natl. Acad. Sci. USA* 86:5673–5677; Loh et al. (1989) *Science* 243:217–220). Products generated by the 3' and 5' RACE procedures can be combined to generate full-length cDNAs (Frohman and Martin (1989) *Techniques* 1:165). Consequently, a polynucleotide comprising a nucleotide sequence of at least 60 (preferably at least 40, most preferably at least 30) contiguous nucleotides derived from a nucleotide sequence selected from the group consisting of SEQ ID NOs:1, 3, 5, 7, 9, 11, 13, and the complement of such nucleotide sequences may be used in such methods to obtain a nucleic acid fragment encoding a substantial portion of an amino acid sequence of a polypeptide. The present invention relates to a method of obtaining a nucleic acid fragment encoding a substantial portion of a polypeptide of a gene (such as plant lecithin-:cholesterol acyltransferases) preferably a substantial portion of a plant polypeptide of a gene, comprising the steps of: synthesizing an oligonucleotide primer comprising a nucleotide sequence of at least one of 60 (preferably at least one of 40, most preferably at least one of 30) contiguous nucleotides derived from a nucleotide sequence selected from the group consisting of SEQ ID NOs:1, 3, 5, 7, 9, 11, and 13, and the complement of such nucleotide sequences; and amplifying a nucleic acid fragment (preferably a cDNA inserted in a cloning vector) using the oligonucleotide primer. The amplified nucleic acid fragment preferably will encode a portion of a polypeptide.

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polygonal or monoclonal antibodies with specificity for peptides or proteins comprising the amino acid sequences. These antibodies can be then be used to screen cDNA expression libraries to isolate full-length cDNA clones of interest (Lerner (1984) *Adv. Immunol.* 36:1–34; Maniatis).

The nucleic acid fragments of the instant invention may be used to create transgenic plants in which the disclosed polypeptides are present at higher or lower levels than normal or in cell types or developmental stages in which they are not normally found. This would have the effect of altering the level of, and composition of, plant sterols in those cells. Since plant sterols help regulate membrane fluidity, this may be beneficial in regulating cold or heat tolerance in plants. Also, it is believed that lecithin is the acyl donor for this reaction, therefore the levels of lecithin found in the plants could be altered by varying the activity of LCAT.

Overexpression of the proteins of the instant invention may be accomplished by first constructing a chimeric gene in which the coding region is operably linked to a promoter capable of directing expression of a gene in the desired tissues at the desired stage of development. For reasons of convenience, the chimeric gene may comprise promoter sequences and translation leader sequences derived from the same genes. 3' Noncoding sequences encoding transcription termination signals may also be provided. The instant chimeric gene may also comprise one or more introns in order to facilitate gene expression.

Plasmid vectors comprising the instant chimeric gene can then be constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al. (1985) *EMBO J.* 4:2411–2418; De Almeida et al. (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant polypeptide to different cellular compartments, or to facilitate its secretion from the cell. It is thus envisioned that the chimeric gene described above may be further supplemented by altering the coding sequence to encode the instant polypeptide with appropriate intracellular targeting sequences such as transit sequences (Keegstra (1989) *Cell* 36:247–253), signal sequences or sequences encoding endoplasmic reticulum localization (Chrispeels (1991) *Ann. Rev. Plant Phys. Plant Mol. Biol.* 42:21–53), or nuclear localization signals (Raikhel (1992) *Plant Phys.* 100: 1627–1632) added and/or with targeting sequences that are already present removed. While the references cited give examples of each of these, the list is not exhaustive and more targeting signals of utility may be discovered in the future.

It may also be desirable to reduce or eliminate expression of genes encoding the instant polypeptides in plants for some applications. In order to accomplish this, a chimeric gene designed for co-suppression of the instant polypeptide can be constructed by linking a gene or gene fragment encoding that polypeptide to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppression technologies in order to reduce expression of particular genes. For example, the proper level of expression of sense or antisense genes may require the use of different chimeric genes utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds, and is not an inherent part of the invention. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

The instant polypeptide (or portions thereof) may be produced in heterologous host cells, particularly in the cells of microbial hosts, and can be used to prepare antibodies to the these proteins by methods well known to those skilled in the art. The antibodies are useful for detecting the polypeptide of the instant invention in situ in cells or in vitro in cell extracts. Preferred heterologous host cells for production of the instant polypeptide are microbial hosts. Microbial expression systems and expression vectors containing regulatory sequences that direct high level expression of foreign proteins are well known to those skilled in the art. Any of these could be used to construct a chimeric gene for production of the instant polypeptide. This chimeric gene could then be introduced into appropriate microorganisms via transformation to provide high level expression of the encoded plant lecithin:cholesterol acyltransferases. An example of a vector for high level expression of the instant polypeptide in a bacterial host is provided (Example 6).

Additionally, the instant polypeptide can be used as a targets to facilitate design and/or identification of inhibitors of those enzymes that may be useful as herbicides. This is desirable because the polypeptide described herein catalyze steps in sterol modification in plants. The composition of plant sterols are important factors in a plants ability to adapt to temperature changes in the environment, shifts in sunlight, and drought stress. In addition, the sterol derivative hormones, such as brassinosteroids, can affect overall growth and development of plants (Szekeres et al. (1996) *Cell* 85:171–182; Clouse and Sasse (1998) *Ann Rev Plant Physiol Plant Mol Biol* 49:427–451). Brassinosteroid production may be affected by changes in composition of membrane sterols. Accordingly, inhibition of the activity of one or more of the enzymes described herein could lead to inhibition of plant growth. Thus, the instant polypeptide could be appropriate for new herbicide discovery and design.

All or a substantial portion of the nucleic acid fragments of the instant invention may also be used as probes for genetically and physically mapping the genes that they are a part of, and as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) *Genomics* 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) *Am. J. Hum. Genet.* 32:314–331).

The production and use of plant gene-derived probes for use in genetic mapping is described in Bernatzky and Tanksley (1986) *Plant Mol. Biol. Reporter* 4:37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: *Nonmammalian Genomic Analysis: A Practical Guide*, Academic press 1996, pp. 319–346, and references cited therein).

In another embodiment, nucleic acid probes derived from the instant nucleic acid sequences may be used in direct fluorescence in situ hybridization (FISH) mapping (Trask (1991) *Trends Genet.* 7:149–154). Although current methods of FISH mapping favor use of large clones (several to several hundred KB; see Laan et al. (1995) *Genome Res.* 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med.* 11:95–96), polymorphism of PCR-amplified fragments (CAPS; Sheffield et al. (1993) *Genomics* 16:325–332), allele-specific ligation (Landegren et al. (1988) *Science* 241:1077–1080), nucleotide extension reactions (Sokolov (1990) *Nucleic Acid Res.* 18:3671), Radiation Hybrid Mapping (Walter et al. (1997) *Nat. Genet.* 7:22–28) and Happy Mapping (Dear and Cook (1989) *Nucleic Acid Res.* 17:6795–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) *Proc. Natl. Acad. Sci USA* 86:9402–9406; Koes et al. (1995) *Proc. Natl. Acad. Sci USA* 92:8149–8153; Bensen et al. (1995) *Plant Cell* 7:75–84). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the instant polypeptide. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding the instant polypeptide can be identified and obtained. This mutant plant can then be used to determine or confirm the natural function of the instant polypeptide disclosed herein.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1

Composition of cDNA Libraries: Isolation and Sequencing of cDNA Clones cDNA libraries representing mRNAs from various corn and soybean tissues were prepared. The characteristics of the libraries are described below.

TABLE 2 cDNA Libraries from Corn and Soybean

| Library | Tissue | Clone |
|---|---|---|
| cbn10 | Corn Developing Kernel 10 Days After Pollination | cbn10.pk0052.g10 |
| cbn2 | Corn Developing Kernel Two Days After Pollination | cbn2.pk0017.h4 |
| p0016 | Corn Embryo 13 Days After Pollination | p0016.ctsbo30r |
| p0018 | Corn Ear Shoot | p0018.chstj36r |
| cen3n | Corn Endosperm 20 Days After Pollination* | cen3n.pk0141.f2:fis |
| cep1c | Corn (Zea mays L.) pollinated (25 hrs after pollination, 48–72 after emergence) ears | cep1c.pk001.f7:fis |
| chpc24 | Corn (MBS847) 8 Day Old Shoot Treated 24 Hours With PDO Herbicide MK593** | chpc24.pk0001.c1 |
| s12 | Soybean Two-Week-Old Developing Seedlings Treated With 2.5 ppm chlorimuron | s12.pk0015.e8:fis |

*This library was normalized essentially as described in U.S. Pat. No. 5,482,845, incorporated herein by reference.
**Application of 2-[(2,4-dihydro-2,6,9-trimethyl[1]benzothiopyrano[4,3-c]pyrazol-8-yl)carbonyl]-1,3-cyclohexanedione S,S-dioxide; synthesis and methods of using this compound are described in WO 97/19087, incorporated herein by reference.

cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are convened into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) Science 252:1651–1656). The resulting ESTs are analyzed using a Perkin Elmer Model 377 fluorescent sequencer.

Example 2

Identification of cDNA Clones cDNA clones encoding plant lecithin:cholesterol acyltransferases were identified by conducting BLAST (Basic Local Alignment Search Tool; Altschul et al. (1993) J. Mol. Biol. 215:403–410) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) Nat. Genet. 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

Example 3

Characterization of cDNA Clones Encoding Lecithin:Cholesterol Acyltransferases

The BLASTX search using the nucleotide sequences from clones cep1c.pk001.f7 and s12.pk0015.e8 and the nucleotide sequences from the contig assembled of clones chpc24.pk0001.c1, cbn2.pk0017.h4, cbn10.pk0052.g10, p0016.ctsbo30r and p0018.chstj36r revealed similarity of the proteins encoded by the cDNAs to lecithin:cholesterol acyltransferase from Homo sapiens (NCBI gi Accession No. 998999) and from rattus norvegicus (NCBI gi Accession No. 418623). The BLAST results for each of these sequences are shown in Table 3:

TABLE 3

BLAST Results for Clones Encoding Polypeptides Homologous to Lecithin:Cholesterol Acyltransferases

| | | Blast pLog Score | |
|---|---|---|---|
| Clone | Status | 98999 | 418623 |
| cep1c.pk001.f7 | EST | 16.40 | 13.40 |
| Contig of:<br>chpc24.pk0001.c1<br>cbn2.pk0017.h4<br>cbn10.pk0052.g10<br>p0016.ctsbo30r<br>p0018.chstj36r | Contig | 12.10 | 14.00 |
| s12.pk0015.e8 | EST | 44.00 | 42.05 |

The sequence of a portion of the cDNA insert from clone cep1c.pk001.f7 is shown in SEQ ID NO:1; the deduced amino acid sequence of this cDNA is shown in SEQ ID NO:2. The sequence of a contig assembled of the cDNA inserts from clones chpc24.pk0001.c1, cbn2.pk0017.h4, cbn10.pk0052.g10, p0016.ctsbo30r and p0018.chstj36r is shown in SEQ ID NO:3; the deduced amino acid sequence of this contig is shown in SEQ ID NO:4. The sequence of the entire cDNA insert in clone s12.pk0015.e8 was determined and is shown in SEQ ID NO:5; the deduced amino acid sequence of this cDNA is shown in SEQ ID NO:6. The amino acid sequence set forth in SEQ ID NO:6 was evaluated by BLASTP, yielding a pLog value of 47.30 versus the Homo sapiens sequence. The soybean lecithin:cholesterol acyltransferase is 32.2% identical to the Homo sapiens sequence. Sequence percent identity calculations were performed by the Jotun Hein method (Hein, J. J. (1990) Meth. Enz. 183:626–645) using the Megalign program of the LASARGENE bioinformatics computing suite (DNASTAR Inc., Madison, Wis.) with the default parameters for pairwise alignment (ktuple=2). BLAST scores and probabilities indicate that the instant nucleic acid fragments encode portions of corn lecithin:cholesterol acyltransferase and an almost entire soybean lecithin:cholesterol acyltransferases. These sequences represent the first plant sequences encoding lecithin:cholesterol acyltransferases.

After the filing of the provisional application (U.S. Provisional Application No. 60/110782, filed Dec. 3, 1998) an Arabidopsis thaliana gene was discovered in the NCBI database (with a deposit date of Dec. 1, 1998). The BLASTX search using the EST sequences from clones listed in Table 4 revealed similarity of the polypeptides encoded by the cDNAs to lecithin:cholesterol acyltransferases from Arabidopsis thaliana (NCBI Accession No. gi 3935185). Shown in Table 4 are the BLAST results for individual ESTs ("EST"), the sequences of the entire cDNA inserts comprising the indicated cDNA clones ("FIS"), contigs assembled from two or more ESTs ("Contig"), contigs assembled from an FIS and one or more ESTs ("Contig*"), or sequences encoding the entire protein derived from an FIS, a contig, or an FIS and PCR ("CGS"):

TABLE 4

BLAST Results for Sequences Encoding Polypeptides Homologous to Lecithin:Cholesterol Acyltransferases

| Clone | Status | BLAST pLog Score<br>3935185 |
|---|---|---|
| cen3n.pk0141.f2:fis | CGS | 63.70 |
| cep1c.pk001.f7:fis | CGS | 84.00 |

TABLE 4-continued

BLAST Results for Sequences Encoding Polypeptides Homologous to Lecithin:Cholesterol Acyltransferases

| Clone | Status | BLAST pLog Score<br>3935185 |
|---|---|---|
| chpc24.pk0001.c1 | FIS | 64.52 |
| s12.pk0015.e8:fis | CGS | 152.00 |

FIGS. 1A and 1B present an alignment of the amino acid sequences set forth in SEQ ID NOs:8, 10, 12, and 14, and the Arabidopsis thaliana sequence (SEQ ID NO:15). The data in Table 4 represents a calculation of the percent identity of the amino acid sequences set forth in SEQ ID NOs:8, 10, 12, and 14, an the Arabidopsis thaliana sequence (SEQ ID NO:15).

TABLE 4

Percent Identity of Amino Acid Sequences Deduced From the Nucleotide Sequences of cDNA Clones Encoding Polypeptides Homologous to Lecithin:Cholesterol Acyltransferases

| SEQ ID NO. | Percent Identity to<br>3935185 |
|---|---|
| 8 | 29.4% |
| 10 | 37.2% |
| 12 | 28.5% |
| 14 | 57.6% |

Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) CABIOS. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of a lecithin:cholesterol acyltransferases. These sequences represent the first plant sequences encoding lecithin:cholesterol acyltransferases.

Example 4

Expression of Chimeric Genes in Monocot Cells

A chimeric gene comprising a cDNA encoding the instant polypeptide in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, Va. 20110-2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf (+) (Promega). Vector and insert DNA can be ligated at 15° C. overnight, essentially as described (Maniatis). The ligated DNA may then be used to transform *E. coli* XL1-Blue (Epicurian Coli XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding the instant polypeptide, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mn long. The embryos are then placed with the axis-side facing down and in contact with agarose-solidified N6 medium (Chu et al. (1975) *Sci. Sin. Peking* 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810–812) and the 3' region of the nopaline synthase gene from the T-DNA of the Ti plasmid of *Agrobacterium tumefaciens.*

The particle bombardment method (Klein et al. (1987) *Nature* 327:70–73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton™ flying disc (Bio-Rad Labs). The particles are then accelerated into the corn tissue with a Biolistic™ PDS-1000/He (Bio-Rad instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when subcultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) *Bio/Technology* 8:833–839).

Example 5

Expression of Chimeric Genes in Dicot Cells

A seed-specific expression cassette composed of the promoter and transcription terminator from the gene encoding the β subunit of the seed storage protein phaseolin from the bean *Phaseolus vulgaris* (Doyle et al. (1986) *J. Biol. Chem.* 261:9228–9238) can be used for expression of the instant polypeptide in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites NcoI (which includes the ATG translation initiation codon), SmaI, KpnI and XbaI. The entire cassette is flanked by HindIII sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embryos may then be transformed with the expression vector comprising sequences encoding the instant polypeptide. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can maintained in 35 mL liquid media on a rotary shaker, 150 rpm, at 26° C. with fluorescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) *Nature* (London) 327:70–73, U.S. Pat. No. 4,945,050). A DuPont Biolistic™ PDS1000/HE instrument (helium retrofit) can be used for these transformations.

A selectable marker gene which can be used to facilitate soybean transformation is a chimeric gene composed of the 35S promoter from Cauliflower Mosaic Virus (Odell et al. (1985) *Nature* 313:810–812), the hygromycin phosphotransferase gene from plasmid pJR225 (from *E. coli*; Gritz et al.(1983) *Gene* 25:179–188) and the 3' region of the nopaline synthase gene from the T-DNA of the Ti plasmid of *Agrobacterium tumefaciens*. The seed expression cassette comprising the phaseolin 5' region, the fragment encoding the instant polypeptide and the phaseolin 3' region can be isolated as a restriction fragment. This fragment can then be inserted into a unique restriction site of the vector carrying the marker gene.

To 50 µL of a 60 mg/mL 1 µm gold particle suspension is added (in order): 5 µL DNA (1 µg/µL), 20 µl spermidine (0.1 M), and 50 µL CaCl$_2$ (2.5 M). The particle preparation is then agitated for three minutes, spun in a microfuge for 10 seconds and the supernatant removed. The DNA-coated particles are then washed once in 400 µL 70% ethanol and resuspended in 40 µL of anhydrous ethanol. The DNA/particle suspension can be sonicated three times for one second each. Five µL of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 6

Expression of Chimeric Genes in Microbial Cells

The cDNAs encoding the instant polypeptide can be inserted into the T7 *E. coli* expression vector pBT430. This vector is a derivative of pET-3a (Rosenberg et al. (1987) *Gene* 56:125–135) which employs the bacteriophage T7 RNA polymerase/T7 promoter system. Plasmid pBT430 was constructed by first destroying the EcoRI and HindIII sites in pET-3a at their original positions. An oligonucleotide adaptor containing EcoRI and HindIII sites was inserted at the BamHI site of pET-3a This created pET-3aM with additional unique cloning sites for insertion of genes into the expression vector. Then, the NdeI site at the position of translation initiation was converted to an NcoI site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTG™ low melting agarose gel (FMC). Buffer and agarose contain 10 µg/ml ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 µL of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkine phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 µg/mL ampicillin. Transformants containing the gene encoding the instant polypeptide are then screened for the correct orientation with respect to the T7 promoter by restriction enzyme analysis.

For high level expression, a plasmid clone with the cDNA insert in the correct orientation relative to the T7 promoter can be transformed into *E. coli* strain BL21(DE3) (Studier et al. (1986) *J. Mol. Biol.* 189:113–130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 µL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One µg of protein from the soluble fraction of the culture can be separated by SDS-polyacrylamide gel electrophoresis. Gels can be observed for protein bands migrating at the expected molecular weight.

Example 7

Evaluating Compounds for Their Ability to inhibit the Activity of Lecithin:Cholesterol Acyltransferases The polypeptide described herein may be produced using any number of methods known to those skilled in the art. Such methods include, but are not limited to, expression in bacteria as described in Example 6, or expression in eukaryotic cell culture, inplanta, and using viral expression systems in suitably infected organisms or cell lines. The instant polypeptide may be expressed either as mature forms of the proteins as observed in vivo or as fusion proteins by covalent attachment to a variety of enzymes, proteins or affinity tags.

Common fusion protein partners include glutathione S-transferase ("GST"), thioredoxin ("Trx"), maltose binding protein, and C- and/or N-terminal hexahistidine polypeptide ("(His)$_6$"). The fusion proteins may be engineered with a protease recognition site at the fusion point so that fusion partners can be separated by protease digestion to yield intact mature enzyme. Examples of such proteases include thrombin, enterokinase and factor Xa. However, any protease can be used which specifically cleaves the peptide connecting the fusion protein and the enzyme.

Purification of the instant polypeptide, if desired, may utilize any number of separation technologies familiar to those skilled in the art of protein purification. Examples of such methods include, but are not limited to, homogenization, filtration, centrifugation, heat denaturation, ammonium sulfate precipitation, desalting, pH precipitation, ion exchange chromatography, hydrophobic interaction chromatography and affinity chromatography, wherein the affinity ligand represents a substrate, substrate analog or inhibitor. When the instant polypeptide are expressed as fusion proteins, the purification protocol may include the use of an affinity resin which is specific for the fusion protein tag attached to the expressed enzyme or an affinity resin containing ligands which are specific for the enzyme. For example, the instant polypeptide may be expressed as a fusion protein coupled to the C-terminus of thioredoxin. In addition, a (His)$_6$ peptide may be engineered into the N-terminus of the fused thioredoxin moiety to afford additional opportunities for affinity purification. Other suitable affinity resins could be synthesized by linking the appropriate ligands to any suitable resin such as Sepharose-4B. In an alternate embodiment, a thioredoxin fusion protein may be eluted using dithiothreitol; however, elution may be accomplished using other reagents which interact to displace the thioredoxin from the resin. These reagents include β-mercaptoetianol or other reduced thiol. The eluted fusion protein may be subjected to further purification by traditional means as stated above, if desired. Proteolytic cleavage of the thioredoxin fusion protein and the enzyme may be accomplished after the fusion protein is purified or while the protein is still bound to the ThioBond™ affinity resin or other resin.

Crude, partially purified or purified enzyme, either alone or as a fusion protein, may be utilized in assays for the evaluation of compounds for their ability to inhibit enzymatic activation of the instant polypeptide disclosed herein. Assays may be conducted under well known experimental conditions which permit optimal enzymatic activity. For example, assays for lecithin:cholesterol acyltransferases are presented by Manabe, M. et al. (1987) *J. Lipid Res.* 28:1206–1215.

Various modifications of the invention in addition to those shown and described herein will be apparent to those skilled in the art from the foregoing description. Such modifications are also intended to fall within the scope of the appended claims.

The disclosure of each reference set forth above is incorporated herein by reference in its entirety.

What is claimed is:

1. An isolated polynucleotide comprising: (a) a nucleic acid sequence encoding a polypeptide having plant lecithin:cholesterol acyltransferase activity, wherein the polypeptide has an amino acid sequence of at least 80% sequence identity, based on the Clustal method of alignment, when compared to SEQ ID NO:14; or (b) a complement of the nucleic acid sequence wherein the complement and the nucleic acid sequence consist of the same number of nucleotides and are 100% complementary.

2. The polynucleotide of claim 1 wherein the amino acid sequence of the polypeptide and the amino acid sequence of SEQ ID NO:14 have at least 95% identity based on the Clustal alignment method.

3. The polynucleotide of claim 1 wherein the polypeptide comprises the nucleic acid sequence of SEQ ID NO:14.

4. The polynucleotide of claim 1 wherein the polynucleotide comprises the nucleic acid sequence of SEQ ID NO:13.

5. A cell or virus comprising the polynucleotide of claim 1.

6. The cell of claim 5 wherein the cell is selected from the group consisting of a yeast cell, a bacterial cell, an insect cell, and a plant cell.

7. A transgenic plant comprising the polynucleotide of claim 1.

8. A method for transforming a cell comprising introducing into a cell the polynucleotide of claim 1.

9. A method for producing a transgenic plant comprising (a) transforming a plant cell with the polynucleotide of claim 1, and (b) regenerating a transgenic plant from the transformed plant cell.

10. A recombinant DNA construct comprising the polynucleotide of claim 1 operably linked to at least one regulatory sequence.

11. The recombinant DNA construct of claim 10, wherein the recombinant DNA construct is an expression vector.

12. A method for increasing the level of plant lecithin:cholesterol acyltransferase polypeptide in a host cell, the method comprising:

a) transforming a host cell with the recombinant DNA construct of claim 11; and b) growing the transformed cell in step (a) under conditions suitable for the expression of the recombinant DNA construct wherein expression of the recombinant DNA construct results in increased expression of the lecithin:cholesterol acyltransferase polypeptide in the transformed host cell.

13. A vector comprising the polynucleotide of claim 1.

14. A method for transforming a cell comprising transforming a cell with the polynucleotide of claim 1.

* * * * *

UNITED STATES PATENT AND TRADEMARK OFFICE
CERTIFICATE OF CORRECTION

PATENT NO. : 6,940,003 B1
DATED : September 6, 2005
INVENTOR(S) : Butler Karlene H. and Kinney Anthony J.

It is certified that error appears in the above-identified patent and that said Letters Patent is hereby corrected as shown below:

<u>Title page,</u>
Item [54], Title, please delete "PLAN" and insert therefor -- PLANT --.

<u>Column 49,</u>
Line 29, please delete "80%" and insert therefor -- 90% --.

Signed and Sealed this

Eighth Day of November, 2005

JON W. DUDAS
*Director of the United States Patent and Trademark Office*

SEQUENCE LISTING

```
<160> NUMBER OF SEQ ID NOS: 15

<210> SEQ ID NO 1
<211> LENGTH: 542
<212> TYPE: DNA
<213> ORGANISM: Zea mays
<220> FEATURE:
<221> NAME/KEY: unsure
<222> LOCATION: (433)
<223> OTHER INFORMATION: n=A, C, G, or T
<220> FEATURE:
<221> NAME/KEY: unsure
<222> LOCATION: (445)
<223> OTHER INFORMATION: n=A, C, G, or T
<220> FEATURE:
<221> NAME/KEY: unsure
<222> LOCATION: (472)
<223> OTHER INFORMATION: n=A, C, G, or T
<220> FEATURE:
<221> NAME/KEY: unsure
<222> LOCATION: (482)
<223> OTHER INFORMATION: n=A, C, G, or T
<220> FEATURE:
<221> NAME/KEY: unsure
<222> LOCATION: (495)
<223> OTHER INFORMATION: n=A, C, G, or T
<220> FEATURE:
<221> NAME/KEY: unsure
<222> LOCATION: (508)
<223> OTHER INFORMATION: n=A, C, G, or T
<220> FEATURE:
<221> NAME/KEY: unsure
<222> LOCATION: (513)
<223> OTHER INFORMATION: n=A, C, G, or T
<220> FEATURE:
<221> NAME/KEY: unsure
<222> LOCATION: (535)
<223> OTHER INFORMATION: n=A, C, G, or T
```

-continued

<400> SEQUENCE: 1

```
gtggcgcaca gctacggcgg cacgctggcg caccagttcc tactgcggcg gcccttgccg     60
tggcgcaggc gcttcgtccg gcggttcgtg cccgttgccg caccgtgggg aggcgtcgtc    120
cttggcatgc tgacaatcgt cgccggcaac aatctcggcc tgccgttcgt cgacccgctg    180
gcgctcaagg gcgagtaccg gagcctgcag agcagcctct ggccgctgcc caaccccaac    240
gcatttagag ccgggcagcc actggtgacc acacggagca ggacgtacac ggcccacgac    300
atggcggact cctcgacgc catcgggcta ggcgcggcaa ttgtgccgta ccagtcccgc     360
gtgctgcccc tgttccggga gctgccatct ccgcgggtgc ccgtggcttg tgtccgtccg    420
gggttgggct ggcacgccg ggaanatgct ggcctaaccc gggaagacga anttcgacgt     480
gnacgcccat tgatnggcaa tggggaaanac ggngaacggg ctgggtcaaa cctgntgaac    540
ct                                                                    542
```

<210> SEQ ID NO 2
<211> LENGTH: 143
<212> TYPE: PRT
<213> ORGANISM: Zea mays

<400> SEQUENCE: 2

```
Val Ala His Ser Tyr Gly Gly Thr Leu Ala His Gln Phe Leu Leu Arg
  1               5                  10                  15

Arg Pro Leu Pro Trp Arg Arg Arg Phe Val Arg Arg Phe Val Pro Val
                 20                  25                  30

Ala Ala Pro Trp Gly Gly Val Val Leu Gly Met Leu Thr Ile Val Ala
             35                  40                  45

Gly Asn Asn Leu Gly Leu Pro Phe Val Asp Pro Leu Ala Leu Lys Gly
         50                  55                  60

Glu Tyr Arg Ser Leu Gln Ser Ser Leu Trp Pro Leu Pro Asn Pro Asn
 65                  70                  75                  80

Ala Phe Arg Ala Gly Gln Pro Leu Val Thr Thr Arg Ser Arg Thr Tyr
                 85                  90                  95

Thr Ala His Asp Met Ala Asp Phe Leu Asp Ala Ile Gly Leu Gly Ala
            100                 105                 110

Ala Ile Val Pro Tyr Gln Ser Arg Val Leu Pro Leu Phe Arg Glu Leu
        115                 120                 125

Pro Ser Pro Arg Val Pro Val Ala Cys Val Arg Pro Gly Leu Gly
    130                 135                 140
```

<210> SEQ ID NO 3
<211> LENGTH: 921
<212> TYPE: DNA
<213> ORGANISM: Zea mays
<220> FEATURE:
<221> NAME/KEY: unsure
<222> LOCATION: (884)
<223> OTHER INFORMATION: n=A, C, G, or T

<400> SEQUENCE: 3

```
cgcagtagaa gatcgagtga gaagttgcgc gtgtgaagcc atcacaccaa ttaaagatcg     60
agatcatcca tggctagttc tctacttcag cagctgctgt ctctgctgct gctcctgctg    120
ccctctcctc ttcgtctccg ggagcatcta tcaggaaacc atgctgtcag cgccaacaac    180
ttccacccca tctttctggt agctggggtg agctgcagcg acctggaggc acgcctcacc    240
gaggagtacc ggccgtcggt gccgcactgc ggcgccatga aggggaaggg gtggttcggt    300
```

```
ctgtggaaga acagttcgga gctgctgtct cgtgactacg tgcagtgctt cgaggagcag    360
atgagcctcg tctacgaccc tgccatcaac gagtaccgga acctcgccgg cgtcgagacg    420
cgagtgccca acttcggctc cacaagagcc ttcagccaca agaaccccct caagtcagac    480
tggtgcctcg gaaagctgag agccgcactg aagacatgg gataccgaga cggagacacc     540
atgttcggag cccctacga cttccgctac gcgccgccgt cccccggcca gacgtccgag     600
gtgtactccc gctacttcaa ggagctgatg gagctggtcg aggccgcgag cgagaggacc    660
cggaagaagg ccgtcatcct cggccacagc ttcggcggca tggtcgcgct cgagttcgtc    720
cggaacactc cgccggcgtg gcggcgcgag cacatcgagc gcctcgtcct ggtcgcgccg    780
acgctccccg gcgggttcct ggagccggtg cgcaacttcg cgtccgggac ggacatcctc    840
tacgtgccag cgacgacgcc gctggccacg cgagccatgt tgangagctt cgagaacgcc    900
atcgtgaatt cccgtcgccg g                                              921
```

<210> SEQ ID NO 4
<211> LENGTH: 233
<212> TYPE: PRT
<213> ORGANISM: Zea mays

<400> SEQUENCE: 4

```
Met Ala Ser Ser Leu Leu Gln Gln Leu Leu Ser Leu Leu Leu Leu Leu
 1               5                  10                  15

Leu Pro Ser Pro Leu Arg Leu Arg Glu His Leu Ser Gly Asn His Ala
            20                  25                  30

Val Ser Ala Asn Asn Phe His Pro Ile Phe Leu Val Ala Gly Val Ser
        35                  40                  45

Cys Ser Asp Leu Glu Ala Arg Leu Thr Glu Glu Tyr Arg Pro Ser Val
    50                  55                  60

Pro His Cys Gly Ala Met Lys Gly Lys Gly Trp Phe Gly Leu Trp Lys
65                  70                  75                  80

Asn Ser Ser Glu Leu Leu Ser Arg Asp Tyr Val Gln Cys Phe Glu Glu
                85                  90                  95

Gln Met Ser Leu Val Tyr Asp Pro Ala Ile Asn Glu Tyr Arg Asn Leu
            100                 105                 110

Ala Gly Val Glu Thr Arg Val Pro Asn Phe Gly Ser Thr Arg Ala Phe
        115                 120                 125

Ser His Lys Asn Pro Leu Lys Ser Asp Trp Cys Leu Gly Lys Leu Arg
    130                 135                 140

Ala Ala Leu Glu Asp Met Gly Tyr Arg Asp Gly Asp Thr Met Phe Gly
145                 150                 155                 160

Ala Pro Tyr Asp Phe Arg Tyr Ala Pro Pro Ser Pro Gly Gln Thr Ser
                165                 170                 175

Glu Val Tyr Ser Arg Tyr Phe Lys Glu Leu Met Glu Leu Val Glu Ala
            180                 185                 190

Ala Ser Glu Arg Thr Arg Lys Lys Ala Val Ile Leu Gly His Ser Phe
        195                 200                 205

Gly Gly Met Val Ala Leu Glu Phe Val Arg Asn Thr Pro Pro Ala Trp
        210                 215                 220

Arg Arg Glu His Ile Glu Arg Leu Val
225                 230
```

<210> SEQ ID NO 5
<211> LENGTH: 1217

-continued

```
<212> TYPE: DNA
<213> ORGANISM: Glycine max

<400> SEQUENCE: 5
ctttcatctg cgaatcatgg taccctctca tcaagaaaaa gaatggatgg ttcagacttt      60
ggtttgattc cagtgtcata cttgctcctt tcactcaatg ctttgccgaa cgcatgaccc     120
ttcattacca ccaagaactc gatgattact tcaacactcc tggggttgag acccgggtcc     180
ctcactttgg ttccaccaac tctcttctct atctcaatcc tcgtctcaag catatcaccg     240
gatacatggc acccctggta gattcattac aaaagcttgg ctacgctgat ggtgagactc     300
tgtttggagc cccttatgac tttagatatg gtctagctgc tgaaggtcac ccttcacaag     360
tgggttccaa gttcctcaaa gatctaaaga atttgataga agaagcaagc aattccaata     420
atgggaagcc agtgatactt ctctcccaca gtttaggagg cctatttgtc ctacaactac     480
taaatagaaa ccccccctct tggcgcaaaa aattcatcaa acacttcatt gctctttcag     540
ctccatgggg tggtgctata gacgaaatgt acacctttgc atctggcaac actttgggag     600
tgcccctagt ggacccttta ttagtgaggg atgaacaaag aagctccgag agtaaccttt     660
ggcttttgcc taacccaaaa attttttggtc ctcaaaaacc aatagtgata actccaatta     720
ggccttattc agctcatgac atggttgatt ttctaaaaga cattggtttt cctgaagggg     780
tttatcctta tgaaacacga attctaccct tgatagggaa cataaaagca ccacaagtgc     840
ctataacttg tattatggga acgggagtgg gaaccttgga acattgtttt tatgggaaag     900
gtgattttga tgaacggcca gaaatatcat atggggatgg tgatgaacg gtgaacttgg     960
tgagcttgtt ggcgcttcaa tcactatgga agaggagaa aaatcaatac cttaaagtgg    1020
ttaagataga tggggtgtct catacttcaa tacttaagga tgaagttgca ctaaatgaaa    1080
tagtaggtga gattacttca attaattctc atgctgagct cggtttaagt aatttgtttt    1140
cggggtaaat gatcagggtg tttgaacgac aattatagat tcgttgtctg caaattaaat    1200
tttgtgtggg gagttga                                                   1217

<210> SEQ ID NO 6
<211> LENGTH: 381
<212> TYPE: PRT
<213> ORGANISM: Glycine max

<400> SEQUENCE: 6
```

Phe Ile Cys Glu Ser Trp Tyr Pro Leu Ile Lys Lys Asn Gly Trp
 1               5                  10                  15

Phe Arg Leu Trp Phe Asp Ser Ser Val Ile Leu Ala Pro Phe Thr Gln
            20                  25                  30

Cys Phe Ala Glu Arg Met Thr Leu His Tyr His Gln Glu Leu Asp Asp
        35                  40                  45

Tyr Phe Asn Thr Pro Gly Val Glu Thr Arg Val Pro His Phe Gly Ser
    50                  55                  60

Thr Asn Ser Leu Leu Tyr Leu Asn Pro Arg Leu Lys His Ile Thr Gly
65                  70                  75                  80

Tyr Met Ala Pro Leu Val Asp Ser Leu Gln Lys Leu Gly Tyr Ala Asp
                85                  90                  95

Gly Glu Thr Leu Phe Gly Ala Pro Tyr Asp Phe Arg Tyr Gly Leu Ala
            100                 105                 110

Ala Glu Gly His Pro Ser Gln Val Gly Ser Lys Phe Leu Lys Asp Leu
        115                 120                 125

```
Lys Asn Leu Ile Glu Glu Ala Ser Asn Ser Asn Asn Gly Lys Pro Val
        130                 135                 140
Ile Leu Leu Ser His Ser Leu Gly Gly Leu Phe Val Leu Gln Leu Leu
145                 150                 155                 160
Asn Arg Asn Pro Pro Ser Trp Arg Lys Lys Phe Ile Lys His Phe Ile
                165                 170                 175
Ala Leu Ser Ala Pro Trp Gly Gly Ala Ile Asp Glu Met Tyr Thr Phe
            180                 185                 190
Ala Ser Gly Asn Thr Leu Gly Val Pro Leu Val Asp Pro Leu Leu Val
            195                 200                 205
Arg Asp Glu Gln Arg Ser Ser Glu Ser Asn Leu Trp Leu Leu Pro Asn
210                 215                 220
Pro Lys Ile Phe Gly Pro Gln Lys Pro Ile Val Ile Thr Pro Ile Arg
225                 230                 235                 240
Pro Tyr Ser Ala His Asp Met Val Asp Phe Leu Lys Asp Ile Gly Phe
                245                 250                 255
Pro Glu Gly Val Tyr Pro Tyr Glu Thr Arg Ile Leu Pro Leu Ile Gly
            260                 265                 270
Asn Ile Lys Ala Pro Gln Val Pro Ile Thr Cys Ile Met Gly Thr Gly
            275                 280                 285
Val Gly Thr Leu Glu Thr Leu Phe Tyr Gly Lys Gly Asp Phe Asp Glu
290                 295                 300
Arg Pro Glu Ile Ser Tyr Gly Asp Gly Asp Gly Thr Val Asn Leu Val
305                 310                 315                 320
Ser Leu Leu Ala Leu Gln Ser Leu Trp Lys Glu Lys Asn Gln Tyr
                325                 330                 335
Leu Lys Val Val Lys Ile Asp Gly Val Ser His Thr Ser Ile Leu Lys
            340                 345                 350
Asp Glu Val Ala Leu Asn Glu Ile Val Glu Ile Thr Ser Ile Asn
            355                 360                 365
Ser His Ala Glu Leu Gly Leu Ser Asn Leu Phe Ser Gly
370                 375                 380

<210> SEQ ID NO 7
<211> LENGTH: 1440
<212> TYPE: DNA
<213> ORGANISM: Zea mays

<400> SEQUENCE: 7
gcacgagccg acaacatcat ggcgaggatt ccccaggttc tggcgccgct cctcctcctg      60
ctgctccccg ccggtctccg ggagctgatg atcgaccgcc ggcccctgcc gaagcgctgc     120
cggcgcgagg tcctcctcca cccgctggtg ctggtgcccg gctgacgtg cagcgagctg     180 gacgcgcggc tcacggacgc ctaccgcccc ttccgcgccg cgtgcgatga aggggaaggg     240
ctggttcggc tctggaccaa ctgctccgac ctgcccgcgc accactacgt gcggtgcttc     300
atggagcaga tggccctcgt ctacgacccc gtcgcgaacg actaccggaa cctgcccggc     360
gtcgagacgc gcgtgcgcaa tttcggctcc tcccgaggat tccagaagaa cccggagcac     420
acgacctggt cctggtgctt cgaggtcctc agaaacgagc tggcaagggc cgggtaccgc     480
gacggcgaca ccctgttcgg ggccccgtac gacctccgct acgccccgcc ggtgcccggc     540
cagccatcga ggtcttctcc ggctacttcc gtcggctggc cgagcctcgt cgaggacgcg     600
agccgcaaga accgggggcag gaaggtgatc ctcttcgggc acagcttcgg gggcatggtg     660
gcgctggagt tcgtccggag cactcccatg gcgtggcgag acaggtacat caagcacctc     720
```

```
ttcctcgtcg ccccggtgcc ggcggaaggg ttcgtgaagc cgctgcagta cttcgtctcc    780
gggtccaacc tgatgtacgt cccgacagtc agctcgctcg agcctgcctt taggccgatg    840
tggcggacct tcgagtcctc cctcgtcaac ttccccctccc cagcggtgtt cgggcgcagg    900
ccgctcgtgg tcaccgcgcg gaggaactac tccgcctacg acctggagga cctcctcgtc    960
gccgtcggct acggcgccgg cgtggagccc ttcaggagac gggcggtccc caagatgagc   1020
tacttccagg ccccaatggt gccgaccacg tgcatgaacg gggtgggcaa cgacacgccg   1080
gagcagctcg tctactggga cggcgacttc gacgcgaccc cggagatagt gtacggcgac   1140
ggggacaatt ccatcaattt ggtcagcatg ctggcgttcg acgagaagat gcgccggcag   1200
ccggaacaga acaaggtgta caagtcgatc aagattcgtg gggcccagca cggtactatt   1260
gtgacagacg acacggcgct caagcgggtc atgcacgaaa tccttgaagc gaatcgtagt   1320
taggctactc acaatgggga tttcatgtct ctgtttccaa aaatgccaca tcagatttat   1380
ggatgaatga aataccctct ctcaatagag agtttcatct caaaaaaaaa aaaaaaaaaa   1440
```

<210> SEQ ID NO 8
<211> LENGTH: 434
<212> TYPE: PRT
<213> ORGANISM: Zea mays

<400> SEQUENCE: 8

```
Met Ala Arg Ile Pro Gln Val Leu Ala Pro Leu Leu Leu Leu Leu
 1               5                  10                  15

Pro Ala Gly Leu Arg Glu Leu Met Ile Asp Arg Arg Pro Leu Pro Lys
                20                  25                  30

Arg Cys Arg Arg Glu Val Leu Leu His Pro Leu Leu Val Pro Gly
            35                  40                  45

Leu Thr Cys Ser Glu Leu Asp Ala Arg Leu Thr Asp Ala Tyr Arg Pro
        50                  55                  60

Phe Arg Ala Ala Cys Asp Glu Gly Glu Gly Leu Val Arg Leu Trp Thr
65                  70                  75                  80

Asn Cys Ser Asp Leu Pro Ala His His Tyr Val Arg Cys Phe Met Glu
                85                  90                  95

Gln Met Ala Leu Val Tyr Asp Pro Val Ala Asn Asp Tyr Arg Asn Leu
            100                 105                 110

Pro Gly Val Glu Thr Arg Val Arg Asn Phe Gly Ser Ser Arg Gly Phe
        115                 120                 125

Gln Lys Asn Pro Glu His Thr Thr Trp Ser Trp Cys Phe Glu Val Leu
    130                 135                 140

Arg Asn Glu Leu Ala Arg Ala Gly Tyr Arg Asp Gly Asp Thr Leu Phe
145                 150                 155                 160

Gly Ala Pro Tyr Asp Leu Arg Tyr Ala Pro Val Pro Gly Gln Pro
                165                 170                 175

Ser Arg Ser Ser Pro Ala Thr Ser Val Gly Trp Pro Ser Leu Val Glu
            180                 185                 190

Asp Ala Ser Arg Lys Asn Arg Gly Arg Lys Val Ile Leu Phe Gly His
        195                 200                 205

Ser Phe Gly Gly Met Val Ala Leu Glu Phe Val Arg Ser Thr Pro Met
    210                 215                 220

Ala Trp Arg Asp Arg Tyr Ile Lys His Leu Phe Leu Val Ala Pro Val
225                 230                 235                 240

Pro Ala Glu Gly Phe Val Lys Pro Leu Gln Tyr Phe Val Ser Gly Ser
```

-continued

```
                245                 250                 255
Asn Leu Met Tyr Val Pro Thr Val Ser Ser Leu Glu Pro Ala Phe Arg
                260                 265                 270
Pro Met Trp Arg Thr Phe Glu Ser Ser Leu Val Asn Phe Pro Ser Pro
            275                 280                 285
Ala Val Phe Gly Arg Arg Pro Leu Val Val Thr Ala Arg Arg Asn Tyr
        290                 295                 300
Ser Ala Tyr Asp Leu Glu Asp Leu Leu Val Ala Val Gly Tyr Gly Ala
305                 310                 315                 320
Gly Val Glu Pro Phe Arg Arg Arg Ala Val Pro Lys Met Ser Tyr Phe
                325                 330                 335
Gln Ala Pro Met Val Pro Thr Thr Cys Met Asn Gly Val Gly Asn Asp
                340                 345                 350
Thr Pro Glu Gln Leu Val Tyr Trp Asp Gly Asp Phe Asp Ala Thr Pro
            355                 360                 365
Glu Ile Val Tyr Gly Asp Gly Asp Asn Ser Ile Asn Leu Val Ser Met
        370                 375                 380
Leu Ala Phe Asp Glu Lys Met Arg Arg Gln Pro Glu Gln Asn Lys Val
385                 390                 395                 400
Tyr Lys Ser Ile Lys Ile Arg Gly Ala Gln His Gly Thr Ile Val Thr
                405                 410                 415
Asp Asp Thr Ala Leu Lys Arg Val Met His Glu Ile Leu Glu Ala Asn
            420                 425                 430
Arg Ser
```

<210> SEQ ID NO 9
<211> LENGTH: 1500
<212> TYPE: DNA
<213> ORGANISM: Zea mays
<220> FEATURE:
<221> NAME/KEY: unsure
<222> LOCATION: (536)
<223> OTHER INFORMATION: n=A, C, G, or T

<400> SEQUENCE: 9

```
ggccacagta gccgccggtt gcgatggtcc acgatatggc ttcttgttcc cgtgcggca    60
cgatcgtgct gtccaaattt gcgagcacga cgaggcgcgc accgaagcag ctgccgcccg   120
tggtggtggt gcccgggtac gccaccaacg agctcgacgc gcgcctcacg gagctgtacc   180
acccgtcgtc accgcgctgc gcgcacaagg ggaaaggctg gttccgcctc tacctcaact   240
acacggcgct ggaggacgcc gccgacgtgc gctgyttcgc cgagcagatg gccacggcgt   300
acgacgcggc gtccgacgac taccgcaacg cccagggcgt ggagacccgc gtcccttcct   360
tcggatccac ccgggccttc cgctaccccg acccagaccg gagaaacttc tcgtacatgg   420
acaagttcgt gtcgcggctg gagcggctcg cgtaccgcga cggcgagaac ctgttcggcg   480
cgccctacga cttccggtac gccgtcgccc gccaggcca cccgtcgagg gtcgcngacg   540
ccttcttcgg gcgcctcagg aggctggtag agagggcgag ccgggctaac ggaggagggc   600
cggtgaccat cgtggcgcac agctacggcg gcacggtggc gcaccagttc ctactgcggc   660
ggcccttgcc gtggcgcagg cgcttcgtcc ggcggttcgt gcccgttgcc gcgccgtggg   720
gaggcgtcgt ccttggcatg ctgacaatcg tcgccggcaa caatctcggc ctgccgttcg   780
tcgacccgct ggcgctcaag ggcgagtacc ggagcctgca gagcagcctc tggccgctgc   840
ccaaccccaa cgcatttaga gccgggcagc cactggtgac cacacggagc aggacgtaca   900
```

-continued

```
cggcccacga catggcggac ttcctcgacg ccatcgggct aggcgcggca attgtgccgt    960
accagtcccg cgtgctgccc ctgttccggg agctgccatc tccgcgggtg cccgtggctt   1020
gtgtcgtcgg ggttgggctg acacgccgg agatgctggc ctacccggga gacgacttcg   1080
acgtgacgcc gatgatggtc atgggagacg gcgacgggct ggtcaacctg gtgagcctcc   1140
tcgctgtcga ccctgcgtgg aggcttccta cagcttactt taggatgctc aaggtgcgca   1200
acgtgtcaca cacgggcctc ttcgtggacg atgctgctct cgccgttatc attagcgcca   1260
tcctacgccc caattaataa ttcactcaga catccgtacg tgcaaaactg ttccggaact   1320
tcacgaaaag ttgagataac aaattttcat cgtagcattg taaggaaata ggtggtaagc   1380
tctaaatttt acattattag ttccgattaa gggctaaaca tgagggatgt acctcctgat   1440
ggtactcttt aaaaaaaaaa aaaaaaaaaa aaaaaaaaaa aaaaaaaaaa aaaaaaaaaa   1500
```

<210> SEQ ID NO 10
<211> LENGTH: 417
<212> TYPE: PRT
<213> ORGANISM: Zea mays

<400> SEQUENCE: 10

```
Met Val His Asp Met Ala Ser Cys Ser Arg Gly Gly Thr Ile Val Leu
  1               5                  10                  15

Ser Lys Phe Ala Ser Thr Thr Arg Arg Ala Pro Lys Gln Leu Pro Pro
             20                  25                  30

Val Val Val Val Pro Gly Tyr Ala Thr Asn Glu Leu Asp Ala Arg Leu
         35                  40                  45

Thr Glu Leu Tyr His Pro Ser Ser Pro Arg Cys Ala His Lys Gly Lys
     50                  55                  60

Gly Trp Phe Arg Leu Tyr Leu Asn Tyr Thr Ala Leu Glu Asp Ala Ala
 65                  70                  75                  80

Asp Val Arg Cys Phe Ala Glu Gln Met Ala Thr Ala Tyr Asp Ala Ala
                 85                  90                  95

Ser Asp Asp Tyr Arg Asn Ala Gln Gly Val Glu Thr Arg Val Pro Phe
            100                 105                 110

Phe Gly Ser Thr Arg Ala Phe Arg Tyr Pro Asp Pro Asp Arg Arg Asn
        115                 120                 125

Phe Ser Tyr Met Asp Lys Phe Val Ser Arg Leu Glu Arg Leu Ala Tyr
    130                 135                 140

Arg Asp Gly Glu Asn Leu Phe Gly Ala Pro Tyr Asp Phe Arg Tyr Ala
145                 150                 155                 160

Val Ala Pro Pro Gly His Pro Ser Arg Val Ala Asp Ala Phe Phe Gly
                165                 170                 175

Arg Leu Arg Arg Leu Val Glu Arg Ala Ser Arg Ala Asn Gly Gly Gly
            180                 185                 190

Pro Val Thr Ile Val Ala His Ser Tyr Gly Gly Thr Val Ala His Gln
        195                 200                 205

Phe Leu Leu Arg Arg Pro Leu Pro Trp Arg Arg Phe Val Arg Arg
    210                 215                 220

Phe Val Pro Val Ala Ala Pro Trp Gly Gly Val Val Leu Gly Met Leu
225                 230                 235                 240

Thr Ile Val Ala Gly Asn Asn Leu Gly Leu Pro Phe Val Asp Pro Leu
                245                 250                 255

Ala Leu Lys Gly Glu Tyr Arg Ser Leu Gln Ser Ser Leu Trp Pro Leu
            260                 265                 270
```

-continued

```
Pro Asn Pro Asn Ala Phe Arg Ala Gly Gln Pro Leu Val Thr Thr Arg
        275                 280                 285
Ser Arg Thr Tyr Thr Ala His Asp Met Ala Asp Phe Leu Asp Ala Ile
    290                 295                 300
Gly Leu Gly Ala Ala Ile Val Pro Tyr Gln Ser Arg Val Leu Pro Leu
305                 310                 315                 320
Phe Arg Glu Leu Pro Ser Pro Arg Val Pro Val Ala Cys Val Val Gly
                325                 330                 335
Val Gly Leu Asp Thr Pro Glu Met Leu Ala Tyr Pro Gly Asp Asp Phe
            340                 345                 350
Asp Val Thr Pro Met Met Val Met Gly Asp Gly Asp Gly Leu Val Asn
        355                 360                 365
Leu Val Ser Leu Leu Ala Val Asp Pro Ala Trp Arg Leu Pro Thr Ala
    370                 375                 380
Tyr Phe Arg Met Leu Lys Val Arg Asn Val Ser His Thr Gly Leu Phe
385                 390                 395                 400
Val Asp Asp Ala Ala Leu Ala Val Ile Ile Ser Ala Ile Leu Arg Pro
                405                 410                 415
Asn
```

<210> SEQ ID NO 11
<211> LENGTH: 1660
<212> TYPE: DNA
<213> ORGANISM: Zea mays

<400> SEQUENCE: 11

```
gcacgagcgc agtagaagat cgagtgagaa gttgcgcgtg tgaagccatc acaccaatta      60
aagatcgaga tcatccatgg ctagttctct acttcagcag ctgctgtctc tgctgctgct     120
cctgctgccc tctcctcttc gtctccggga gcatctatca ggaaaccatg ctgtcagcgc     180
caacaacttc caccccatct ttctggtagc tggggtgagc tgcagcgacc tggaggcacg     240
cctcaccgag gagtaccggc cgtcggtgcc gcactgcggc gccatgaagg ggaaggggtg     300
gttcggtctg tggaagaaca gttcggagct gctgtctcgt gactacgtgc agtgcttcga     360
ggagcagatg agcctcgtct acgaccctgc catcaacgag taccggaacc tcgccggcgt     420
cgagacgcga gtgcccaact tcggctccac aagagccttc agccacaaga ccccctcaa     480
gtcagactgg tgcctcggaa agctgagagc cgcactggaa gacatgggat accgagacgg     540
agacaccatg ttcggagccc cctacgactt ccgctacgcg ccgccgtccc ccggccagac     600
gtccgaggtg tactcccgct acttcaagga gctgatggag ctggtcgagg ccgcgagcga     660
gaggacccgg aagaaggccg tcatcctcgg ccacagcttc ggcggcatgg tcgcgctcga     720
gttcgtccgg aacactccgc cggcgtggcg gcgcgagcac atcgagcgcc tcgtcctggt     780
cgcgccgacg ctccccggcg ggttcctgga gccggtgcgc aacttcgcgt ccggacgga     840
catcctctac gtgccagcga cgacgccgct ggccacgcga gccatgtgga ggagcttcga     900
gagcgccatc gtgaacttcc cgtcgccggc cgtgttcggg cgcctgcagg cgccgctcgt     960
ggtcaccagg gagcggaact actccgcgtc cgcgcacgac atggagcgct tcctcgccgc    1020
cgtcggctcc ggcgaggccg cggagcccct caggagacgg gccgtcccca agatgggcag    1080
cttcgcggcg ccgatggtgc ccatgacgta catcagcggg gtcggcaaca ggacgccgct    1140
gcggctggtg ttctggggcg aagacttcga cgcggccccg gaggtggcgg cgtacgggga    1200
ccgagatggc aagatcaatt tgatcagcgt cttggcgttt gagaaggaga tgcgtcggca    1260
```

-continued

```
gccggagcag aagaagcagt tcaaatccat caagatcaat aaggcccagc attctacgat   1320
cgtcacggat gattttgccc tgcacagggt cattcaagaa attgttgagg ccaataatca   1380
gaagattcca tcctaaatta ttcatgtcat gtatgcatta ccgagctgtg ggggccaata   1440
gtgggttggg aagtgatggt ttagacatcg gtcgtggtgt ggtcgcaatt caatcgatta   1500
gttatttgtt aacgtcaatt gcttgcctca tgaacttgct gtgataagga aagaccacaa   1560
ttattttccg cttgtcgtgt gcgttgtacc gtataatgtt aataaaaaca agagtaaaat   1620
atagtagcag tcatcaaact taaaaaaaaa aaaaaaaaa                          1660
```

<210> SEQ ID NO 12
<211> LENGTH: 439
<212> TYPE: PRT
<213> ORGANISM: Zea mays

<400> SEQUENCE: 12

```
Met Ala Ser Ser Leu Leu Gln Gln Leu Leu Ser Leu Leu Leu Leu Leu
 1               5                  10                  15

Leu Pro Ser Pro Leu Arg Leu Arg Glu His Leu Ser Gly Asn His Ala
            20                  25                  30

Val Ser Ala Asn Asn Phe His Pro Ile Phe Leu Val Ala Gly Val Ser
        35                  40                  45

Cys Ser Asp Leu Glu Ala Arg Leu Thr Glu Glu Tyr Arg Pro Ser Val
    50                  55                  60

Pro His Cys Gly Ala Met Lys Gly Lys Gly Trp Phe Gly Leu Trp Lys
65                  70                  75                  80

Asn Ser Ser Glu Leu Leu Ser Arg Asp Tyr Val Gln Cys Phe Glu Glu
                85                  90                  95

Gln Met Ser Leu Val Tyr Asp Pro Ala Ile Asn Glu Tyr Arg Asn Leu
            100                 105                 110

Ala Gly Val Glu Thr Arg Val Pro Asn Phe Gly Ser Thr Arg Ala Phe
        115                 120                 125

Ser His Lys Asn Pro Leu Lys Ser Asp Trp Cys Leu Gly Lys Leu Arg
    130                 135                 140

Ala Ala Leu Glu Asp Met Gly Tyr Arg Asp Gly Asp Thr Met Phe Gly
145                 150                 155                 160

Ala Pro Tyr Asp Phe Arg Tyr Ala Pro Pro Ser Pro Gly Gln Thr Ser
                165                 170                 175

Glu Val Tyr Ser Arg Tyr Phe Lys Glu Leu Met Glu Leu Val Glu Ala
            180                 185                 190

Ala Ser Glu Arg Thr Arg Lys Lys Ala Val Ile Leu Gly His Ser Phe
        195                 200                 205

Gly Gly Met Val Ala Leu Glu Phe Val Arg Asn Thr Pro Pro Ala Trp
    210                 215                 220

Arg Arg Glu His Ile Glu Arg Leu Val Leu Val Ala Pro Thr Leu Pro
225                 230                 235                 240

Gly Gly Phe Leu Glu Pro Val Arg Asn Phe Ala Ser Gly Thr Asp Ile
                245                 250                 255

Leu Tyr Val Pro Ala Thr Thr Pro Leu Ala Thr Arg Ala Met Trp Arg
            260                 265                 270

Ser Phe Glu Ser Ala Ile Val Asn Phe Pro Ser Pro Val Phe Gly
        275                 280                 285

Arg Leu Gln Ala Pro Leu Val Val Thr Arg Glu Arg Asn Tyr Ser Ala
    290                 295                 300
```

```
Ser Ala His Asp Met Glu Arg Phe Leu Ala Ala Val Gly Ser Gly Glu
305                 310                 315                 320
Ala Ala Glu Pro Phe Arg Arg Arg Ala Val Pro Lys Met Gly Ser Phe
                325                 330                 335
Ala Ala Pro Met Val Pro Met Thr Tyr Ile Ser Gly Val Gly Asn Arg
            340                 345                 350
Thr Pro Leu Arg Leu Val Phe Trp Gly Glu Asp Phe Asp Ala Ala Pro
        355                 360                 365
Glu Val Ala Ala Tyr Gly Asp Arg Asp Gly Lys Ile Asn Leu Ile Ser
    370                 375                 380
Val Leu Ala Phe Glu Lys Glu Met Arg Arg Gln Pro Glu Gln Lys Lys
385                 390                 395                 400
Gln Phe Lys Ser Ile Lys Ile Asn Lys Ala Gln His Ser Thr Ile Val
                405                 410                 415
Thr Asp Asp Phe Ala Leu His Arg Val Ile Gln Glu Ile Val Glu Ala
            420                 425                 430
Asn Asn Gln Lys Ile Pro Ser
        435
```

<210> SEQ ID NO 13
<211> LENGTH: 1332
<212> TYPE: DNA
<213> ORGANISM: Glycine max

<400> SEQUENCE: 13

```
atgaagaagg aacaagaaga gggtctcaag attgaggttg ctacactcac agttacagta      60
gttgttgtga tgctgtcatt gctatgcaca tgtggggcaa gcaacctcga ccctttgatt     120
ctaataccag gtaacggagg gaaccaacta gaagcaaggt tgaccaatca gtacaagccc     180
tctactttca tctgcgaatc atggtaccct ctcatcaaga aaagaatgg atggttcaga      240
cttttggttttg attccagtgt catacttgct ccttttcactc aatgctttgc cgaacgcatg     300
acccttcatt accaccaaga actcgatgat tacttcaaca ctcctggggt tgagacccgg     360
gtccctcact ttggttccac caactctctt ctctatctca atcctcgtct caagcatatc     420
accggataca tggcaccct ggtagattca ttacaaaagc ttggctacgc tgatggtgag      480
actctgtttg gagccccta tgactttaga tatggtctag ctgctgaagg tcaccctca      540
caagtgggtt ccaagttcct caaagatcta agaatttga tagaagaagc aagcaattcc     600
aataatggga gccagtgat acttctctcc cacagtttag gaggcctatt tgtcctacaa     660
ctactaaata gaaaccccccc ctcttggcgc aaaaaattca tcaaacactt cattgctctt     720
tcagctccat ggggtggtgc tatagacgaa atgtacacct tgcatctgg caacactttg     780
ggagtgcccc tagtggaccc tttattagtg agggatgaac aaagaagctc cgagagtaac     840
ctttggcttt tgcctaaccc aaaaatttt ggtcctcaaa accaatagt gataactcca      900
attaggcctt attcagctca tgacatggtt gattttctaa aagacattgg ttttcctgaa     960
ggggttattc cttatgaaac acgaattcta cccttgatag gaacataaa agcaccacaa     1020
gtgcctataa cttgtattat gggaacggga gtgggaacct tggaaacatt gttttatggg    1080
aaaggtgatt ttgatgaacg gccagaaata tcatatgggg atggtgatgg aacggtgaac    1140
ttggtgagct tgttggcgct tcaatcacta tggaaagagg agaaaaatca ataccttaaa    1200
gtggttaaga tagatgggt gtctcatact tcaatactta aggatgaagt tgcactaaat     1260
gaaatagtag gtgagattac ttcaattaat tctcatgctg agctcggttt aagtaatttg    1320
```

-continued ttttcggggt aa                                                    1332

<210> SEQ ID NO 14
<211> LENGTH: 443
<212> TYPE: PRT
<213> ORGANISM: Glycine max

<400> SEQUENCE: 14

Met Lys Lys Glu Gln Glu Glu Gly Leu Lys Ile Glu Val Ala Thr Leu
 1               5                  10                  15

Thr Val Thr Val Val Val Met Leu Ser Leu Leu Cys Thr Cys Gly
             20                  25                  30

Ala Ser Asn Leu Asp Pro Leu Ile Leu Ile Pro Gly Asn Gly Gly Asn
         35                  40                  45

Gln Leu Glu Ala Arg Leu Thr Asn Gln Tyr Lys Pro Ser Thr Phe Ile
     50                  55                  60

Cys Glu Ser Trp Tyr Pro Leu Ile Lys Lys Asn Gly Trp Phe Arg
 65                  70                  75                  80

Leu Trp Phe Asp Ser Ser Val Ile Leu Ala Pro Phe Thr Gln Cys Phe
                 85                  90                  95

Ala Glu Arg Met Thr Leu His Tyr His Gln Glu Leu Asp Asp Tyr Phe
            100                 105                 110

Asn Thr Pro Gly Val Glu Thr Arg Val Pro His Phe Gly Ser Thr Asn
        115                 120                 125

Ser Leu Leu Tyr Leu Asn Pro Arg Leu Lys His Ile Thr Gly Tyr Met
    130                 135                 140

Ala Pro Leu Val Asp Ser Leu Gln Lys Leu Gly Tyr Ala Asp Gly Glu
145                 150                 155                 160

Thr Leu Phe Gly Ala Pro Tyr Asp Phe Arg Tyr Gly Leu Ala Ala Glu
                165                 170                 175

Gly His Pro Ser Gln Val Gly Ser Lys Phe Leu Lys Asp Leu Lys Asn
            180                 185                 190

Leu Ile Glu Glu Ala Ser Asn Ser Asn Asn Gly Lys Pro Val Ile Leu
        195                 200                 205

Leu Ser His Ser Leu Gly Gly Leu Phe Val Leu Gln Leu Leu Asn Arg
    210                 215                 220

Asn Pro Pro Ser Trp Arg Lys Lys Phe Ile Lys His Phe Ile Ala Leu
225                 230                 235                 240

Ser Ala Pro Trp Gly Gly Ala Ile Asp Glu Met Tyr Thr Phe Ala Ser
                245                 250                 255

Gly Asn Thr Leu Gly Val Pro Leu Val Asp Pro Leu Leu Val Arg Asp
            260                 265                 270

Glu Gln Arg Ser Ser Glu Ser Asn Leu Trp Leu Leu Pro Asn Pro Lys
        275                 280                 285

Ile Phe Gly Pro Gln Lys Pro Ile Val Ile Thr Pro Ile Arg Pro Tyr
    290                 295                 300

Ser Ala His Asp Met Val Asp Phe Leu Lys Asp Ile Gly Phe Pro Glu
305                 310                 315                 320

Gly Val Tyr Pro Tyr Glu Thr Arg Ile Leu Pro Leu Ile Gly Asn Ile
                325                 330                 335

Lys Ala Pro Gln Val Pro Ile Thr Cys Ile Met Gly Thr Gly Val Gly
            340                 345                 350

Thr Leu Glu Thr Leu Phe Tyr Gly Lys Gly Asp Phe Asp Glu Arg Pro
        355                 360                 365

```
Glu Ile Ser Tyr Gly Asp Gly Asp Gly Thr Val Asn Leu Val Ser Leu
    370                 375                 380

Leu Ala Leu Gln Ser Leu Trp Lys Glu Lys Asn Gln Tyr Leu Lys
385                 390                 395                 400

Val Val Lys Ile Asp Gly Val Ser His Thr Ser Ile Leu Lys Asp Glu
                405                 410                 415

Val Ala Leu Asn Glu Ile Val Gly Glu Ile Thr Ser Ile Asn Ser His
            420                 425                 430

Ala Glu Leu Gly Leu Ser Asn Leu Phe Ser Gly
            435                 440
```

<210> SEQ ID NO 15
<211> LENGTH: 432
<212> TYPE: PRT
<213> ORGANISM: Arabidopsis thaliana

<400> SEQUENCE: 15

```
Met Lys Lys Ile Ser Ser His Tyr Ser Val Val Ile Ala Ile Leu Val
 1               5                  10                  15

Val Val Thr Met Thr Ser Met Cys Gln Ala Val Gly Ser Asn Val Tyr
            20                  25                  30

Pro Leu Ile Leu Val Pro Gly Asn Gly Gly Asn Gln Leu Glu Val Arg
        35                  40                  45

Leu Asp Arg Glu Tyr Lys Pro Ser Ser Val Trp Cys Ser Ser Trp Leu
    50                  55                  60

Tyr Pro Ile His Lys Lys Ser Gly Gly Trp Phe Arg Leu Trp Phe Asp
65                  70                  75                  80

Ala Ala Val Leu Leu Ser Pro Phe Thr Arg Cys Phe Ser Asp Arg Met
                85                  90                  95

Met Leu Tyr Tyr Asp Pro Asp Leu Asp Asp Tyr Gln Asn Ala Pro Gly
            100                 105                 110

Val Gln Thr Arg Val Pro His Phe Gly Ser Thr Lys Ser Leu Leu Tyr
        115                 120                 125

Leu Asp Pro Arg Leu Arg Asp Ala Thr Ser Tyr Met Glu His Leu Val
    130                 135                 140

Lys Ala Leu Glu Lys Lys Cys Gly Tyr Val Asn Asp Gln Thr Ile Leu
145                 150                 155                 160

Gly Ala Pro Tyr Asp Phe Arg Tyr Gly Leu Ala Ala Ser Gly His Pro
                165                 170                 175

Ser Arg Val Ala Ser Gln Phe Leu Gln Asp Leu Lys Gln Leu Val Glu
            180                 185                 190

Lys Thr Ser Ser Glu Asn Glu Gly Lys Pro Val Ile Leu Leu Ser His
        195                 200                 205

Ser Leu Gly Gly Leu Phe Val Leu His Phe Leu Asn Arg Thr Thr Pro
    210                 215                 220

Ser Trp Arg Arg Lys Tyr Ile Lys His Phe Val Ala Leu Ala Ala Pro
225                 230                 235                 240

Trp Gly Gly Thr Ile Ser Gln Met Lys Thr Phe Ala Ser Gly Asn Thr
                245                 250                 255

Leu Gly Val Pro Leu Val Asn Pro Leu Leu Val Arg Arg His Gln Arg
            260                 265                 270

Thr Ser Glu Ser Asn Gln Trp Leu Leu Pro Ser Thr Lys Val Phe His
        275                 280                 285

Asp Arg Thr Lys Pro Leu Val Val Thr Pro Gln Val Asn Tyr Thr Ala
    290                 295                 300
```

-continued

```
Tyr Glu Met Asp Arg Phe Phe Ala Asp Ile Gly Phe Ser Gln Gly Val
305                 310                 315                 320

Val Pro Tyr Lys Thr Arg Val Leu Pro Leu Thr Glu Glu Leu Met Thr
                325                 330                 335

Pro Gly Val Pro Val Thr Cys Ile Tyr Gly Arg Gly Val Asp Thr Pro
                340                 345                 350

Glu Val Leu Met Tyr Gly Lys Gly Gly Phe Asp Lys Gln Pro Glu Ile
            355                 360                 365

Lys Tyr Gly Asp Gly Asp Gly Thr Val Asn Leu Ala Ser Leu Ala Ala
        370                 375                 380

Leu Lys Val Asp Ser Leu Asn Thr Val Glu Ile Asp Gly Val Ser His
385                 390                 395                 400

Thr Ser Ile Leu Lys Asp Glu Ile Ala Leu Lys Glu Ile Met Lys Gln
                405                 410                 415

Ile Ser Ile Ile Asn Tyr Glu Leu Ala Asn Val Asn Ala Val Asn Glu
                420                 425                 430
```